(12) United States Patent
Takenaka et al.

(10) Patent No.: US 7,728,154 B2
(45) Date of Patent: Jun. 1, 2010

(54) PROCESS FOR THE PREPARATION OF 1-ARYL-3,4-DIHYDRO-1H-NAPHTHALENE-2-ONE

(75) Inventors: Junji Takenaka, Shunan (JP); Nobumasa Kuwashima, Shunan (JP); Toshiaki Takahashi, Shunan (JP)

(73) Assignee: Tokuyama Corporation, Shunan-shi (JP)

( * ) Notice: Subject to any disclaimer, the term of this patent is extended or adjusted under 35 U.S.C. 154(b) by 283 days.

(21) Appl. No.: 12/068,446

(22) Filed: Feb. 6, 2008

(65) Prior Publication Data

US 2008/0200697 A1    Aug. 21, 2008

(30) Foreign Application Priority Data

Feb. 7, 2007    (JP) .............................. 2007-028254

(51) Int. Cl.
*C07D 317/44*    (2006.01)

(52) U.S. Cl. ..................................... 549/446

(58) Field of Classification Search .................. 549/446
See application file for complete search history.

(56) References Cited

U.S. PATENT DOCUMENTS 4,296,257 A    10/1981    Cardenas et al.
5,817,890 A    10/1998    Duhamel et al.

OTHER PUBLICATIONS

Jensen et al. Tetrahedron Letters 41, 6029-6033, 2000.*
Misono et al., The Journal of Physical Chemistry, vol. 76, No. 1, 1972, pp. 44-49, XP009103079.
Jensen et al., Tetrahedron Letters, vol. 41, No. 32, pp. 6029-6033, Aug. 5, 2000, XP004243507.

* cited by examiner

*Primary Examiner*—D. Margaret Seaman
*Assistant Examiner*—Nizal S Chandrakumar
(74) *Attorney, Agent, or Firm*—Birch, Stewart, Kolasch & Birch, LLP

(57) ABSTRACT

1-aryl-3,4-dihydro-1H-naphthalene-2-one is prepared by isomerizing an epoxy compound represented by the following general formula,

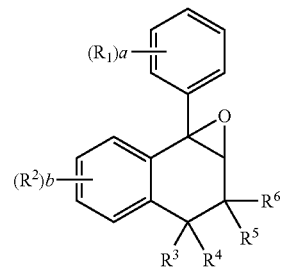

wherein a is an integer of 0 to 5, b is an integer of 0 to 4, and $R^1$ to $R^6$ are hydrogen atoms or substituents such as alkyl groups,
in an organic solvent in the presence of magnesium sulfate. This process makes it possible to prepare the 1-aryl-3,4-dihydro-1H-naphthalene-2-one safely and in a high yield without using highly explosive compounds such as lithium perchlorate.

2 Claims, No Drawings

PROCESS FOR THE PREPARATION OF 1-ARYL-3,4-DIHYDRO-1H-NAPHTHALENE-2-ONE

BACKGROUND OF THE INVENTION

1. Field of the Invention

This invention relates to a process for the preparation of a 1-aryl-3,4-dihydro-1H-naphthalene-2-one.

2. Description of the Related Art

Tetralones are compounds which are very important as intermediate products for synthesizing steroids and various medicinal starting materials. Among the tetralones, 1-tetralones are relatively inexpensive and are industrially and easily available. However, 2-tetralones such as 1-aryl-3,4-dihydro-1H-naphthalene-2-one are prepared through complex production processes and are not easily available. One of the problems involved in the production process thereof is that a special reaction catalyst is necessary for obtaining 2-tetralones from the epoxides which are the starting materials and, besides, a high yield is not attained.

The 1-aryl-3,4-dihydro-1H-naphthalene-2-one has heretofore been prepared by a method in which epoxides are refluxed in benzene in the presence of lithium perchlorate (Prior art 1), a method in which epoxides are refluxed in sulfuric acid solution (Prior art 2), and a method in which epoxides are refluxed in benzene at the presence of zinc iodide or epoxides are agitated in ether at the presence of boron trifluoride ether complex (Prior art 3).

Prior art 1: Australian Journal of Chemistry, 34(7), 1467 (1981)

Prior art 2: Journal of the Organic Chemistry, 15, 1197 (1950)

Prior art 3: Tetrahedron Letters, 41, 6029 (2000)

SUMMARY OF THE INVENTION

According to the method of the prior art 1, however, there is a probability of explosion since the lithium perchlorate and the organic solvent are brought in contact together. The method of the prior art 2 involves many problems such as the formation of byproducts in large amounts and low yields of about 60% at the highest. Besides, in the method disclosed in the prior art 3, zinc iodide is acute toxic substance and boron trifluoride ether complex has extremely strong corrosive nature. Both substances are not appropriate for the industrial application.

The present inventors have conducted a study concerning a novel process for the preparation of 1-aryl-3,4-dihydro-1H-naphthalene-2-one, and have discovered that this compound of which the aryl group is condensed with a 1,3-dioxolan ring is a novel compound and is useful as a starting material for producing chromene compounds having photochromic properties.

It is, therefore, an object of the present invention to provide a process for the preparation of a 1-aryl-3,4-dihydro-1H-naphthalene-2-one safely and in a high yield without using a dangerous compound such as lithium perchlorate.

Another object of the present invention is to provide a 1-aryl-3,4-dihydro-1H-naphthalene-2-one having a novel structure.

According to the present invention, there is provided a process for the preparation of a 1-aryl-3,4-dihydro-1H-naphthalene-2-one represented by the following general formula (1),

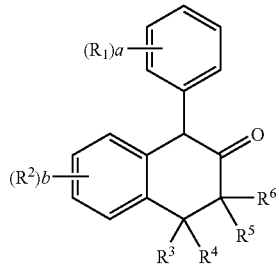

(1)

wherein a is an integer of 0 to 5, b is an integer of 0 to 4, $R^1$ and $R^2$ are alkyl groups, alkoxy groups, aralkoxy groups, substituted amino groups, cyano groups, halogen atoms, aralkyl groups or aryl groups, when a or b is 2 or more, a plurality of $R^1$ or $R^2$ may be different from each other, and two $R^1$ or $R^2$ at adjacent positions may be bonded together to form a divalent group represented by the following formula (1a),

(1a)

wherein $R^7$ and $R^8$ are alkylene groups, and l, m and n are, respectively, integers of 0 to 3 under a condition in which they are not all zero, and $R^3$ to $R^6$ are, respectively, hydrogen atoms, alkyl groups, alkoxy groups, aralkoxy groups, substituted amino groups, cyano groups, halogen atoms, aralkyl groups or aryl groups, comprising:

a step (A) of preparing an epoxy compound represented by the following general formula (2),

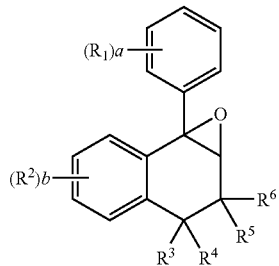

(2)

wherein a, b and $R^1$ to $R^6$ are as defined in the above general formula (1), and a step (B) of isomerizing the epoxy compound in an organic solvent in the presence of magnesium sulfate.

According to the present invention, further, there is provided 1-aryl-3,4-dihydro-1H-naphthalene-2-one represented by the following general formula (1'),

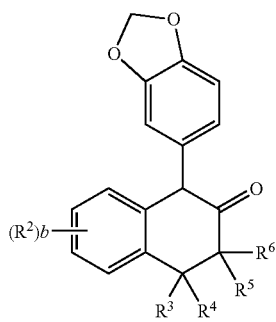

(1')

wherein b, $R^2$, and $R^3$ to $R^6$ are all as defined in the above general formula (1).

The process of the present invention prepares 1-aryl-3,4-dihydro-1H-naphthalene-2-one (hereinafter often simply referred to as 2-tetralone derivative) represented by the above general formula (1) by using the epoxide compound represented by the above general formula (2) as a starting material and isomerizing the epoxide compound in the organic solvent in the presence of magnesium sulfate. According to the above process, the isomerization reaction proceeds without almost forming byproducts, and a 2-tetralone derivative is obtained in a very high yield which can be almost regarded to be quantitative as will become obvious from Examples appearing later.

The process of the present invention can be conducted very stably and industrially as compared to the method of refluxing in benzene in the presence of lithium perchlorate, or as compared to the method of using zinc iodide or boron trifluoride ether complex. The process of the present invention, further, makes it possible to obtain the object product in a high yield forming byproducts in amounts very smaller than that of the method of refluxing in a sulfuric acid solution. According to the above conventional methods, further, the yield decreases strikingly when the epoxy compound which is a starting material has an alkoxy group or an ether bond. The process of the present invention, however, makes it possible to prepare the desired 2-tetralone derivative in a very high yield even when the starting epoxy compound has the alkoxy group or the ether bond.

Among the 2-tetralone derivatives of the general formula (1) obtained by the process of the present invention, further, the compound of the general formula (1') having a condensed ring in which the benzene ring is condensed with a 1,3-dioxolan ring is a novel material, and is useful as a starting material for preparing, particularly, chromene compounds having photochromic properties.

DETAILED DESCRIPTION OF THE INVENTION

<Step (a): Starting Material>

In the present invention, an epoxy compound represented by the general formula (2),

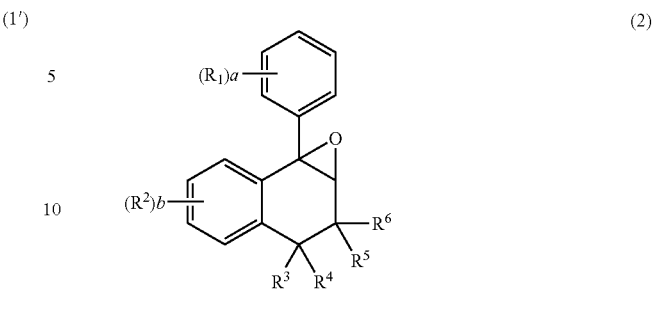

(2)

is used as a starting material.

In the above general formula (2), "a" represents the number of substituents $R^1$ and is an integer of 0 to 5, and "b" represents the number of substituents $R^2$ and is an integer of 0 to 4.

Further, the substituents $R^1$ and $R^2$ are alkyl groups, alkoxy groups, aralkoxy groups, substituted amino groups, cyano groups, halogen atoms, aralkyl groups or aryl groups.

Among the above groups, the alkyl group is, preferably, the one generally having 1 to 6 carbon atoms, such as methyl group, ethyl group, n-propyl group, isopropyl group, n-butyl group, sec-butyl group, t-butyl group, n-hexyl group or cyclohexyl group.

The alkoxy group is, preferably, the one generally having 1 to 6 carbon atoms, such as methoxy group, ethoxy group, n-propoxy group, isopropoxy group, n-butoxy group, sec-butoxy group, t-butoxy group, n-hexyloxy group or cyclohexyloxy group.

The aralkoxy group is, preferably, the one having 6 to 10 carbon atoms, such as phenoxy group or naphthoxy group.

Though there is no particular limitation, the substituted amino group is, preferably, the one having an alkyl group or an aryl group bonded as a substituent to a nitrogen atom, such as alkylamino group, dialkylamino group, arylamino group or diarylamino group. Concrete examples will be methylamino group, ethylamino group, phenylamino group, dimethylamino group, diethylamino group, diphenylamino group, morpholino group, piperidino group, pyrrolidinyl group, piperadino group, N-methylpiperadino group and indolinyl group.

As the halogen atom, there can be exemplified fluorine atom, chlorine atom, bromine atom or iodine atom.

As the aralkyl group, there can be exemplified benzyl group, phenylethyl group, phenylpropyl group or phenylbutyl group. As the aryl group, there can be exemplified phenyl group or naphthyl group. The aralkyl group and the aryl group may have suitable numbers of substituents. As the substituents, there can be exemplified the above-mentioned alkyl group, alkoxy group, aryl group, substituted amino group, halogen atom and aralkyl group.

When the substituents $R^1$ or $R^2$ are present in a plural number (when "a" or "b" are 2 or more), the plurality of $R^1$ or $R^2$ may be different from each other.

In the above substituents $R^1$ or $R^2$, further, the two $R^1$ or $R^2$ at adjacent positions of the benzene ring may be bonded together to form a divalent group represented by the following formula (2a),

(2a)

The divalent group of the formula (2a) is the same as the divalent group represented by the formula (1a) in the general formula (1). When the divalent group is formed, the benzene ring may further have a ring bonded thereto.

In the above formula (2a), $R^7$ and $R^8$ are alkylene groups such as, —$CH_2$—, —$CH_2CH_2$—, or —$CH_2CH_2CH_2$—, and l, m and n are integers of 0 to 3, respectively, under a condition in which they are not all zero.

A representative example of the divalent group will be —O—$CH_2$—O—. In this case, the benzene ring assumes a form of being condensed with the 1,3-dioxolan ring. When the epoxy compound of the structure forming the above divalent group is used as a starting material, the novel 2-tetralone derivative represented by the general formula (1') described below can be produced.

In the general formula (2), $R^3$ to $R^6$ are hydrogen atoms, alkyl groups, alkoxy groups, aralkoxy groups, substituted amino groups, cyano groups, halogen atoms, aralkyl groups or aryl groups. Among these groups, the alkyl groups, alkoxy groups, aralkoxy groups, substituted amino groups, cyano groups, halogen atoms, aralkyl groups and aryl groups are the same as those described concerning the groups $R^1$ and $R^2$.

<Step (b): Isomerization Reaction>

In the present invention, the epoxy compound represented by the above general formula (2) is isomerized in an organic solvent in the presence of magnesium sulfate.

Any organic solvent can be used if it does not hinder the isomerization reaction. Concrete examples include alcohols such as methanol, ethanol, i-butanol and 2-ethoxyethanol; aliphatic hydrocarbons such as hexane, cyclohexane, heptane and i-octane; aromatic hydrocarbons such as toluene, xylene; ketones such as cyclohexanone and methyl ethyl ketone; ethers such as diethyl ether, methyl t-butyl ether, dibenzyl ether and diethylene glycol dimethyl ether; and halogenated hydrocarbons such as chloroform and methylene chloride.

Magnesium sulfate which is an isomerization catalyst is used, usually, in an amount of 0.001 to 30 mols per mol of the starting epoxy compound.

That is, the magnesium sulfate and the organic solvent are mixed to the epoxy compound and are suitably heated, whereby the epoxy compound has its oxirane ring opened and is isomerized into the 2-tetralone structure. In this case, the heating temperature may be about 20 to about 120° C., and the organic solvent may be used in such an amount that the starting epoxy compound uniformly dissolves therein and no excess burden is exerted on removing the solvent. The reaction time is, usually, about 10 minutes to about 300 minutes.

After the reaction, the reaction product is cooled and is suitably washed with water to remove the magnesium sulfate, followed by the condensation under reduced pressure to remove the solvent. Thus, the desired 2-tetralone derivative is obtained in a very high yield.

<2-Tetralone Derivative>

Being corresponded to the structure of the starting epoxy compound represented by the general formula (2), the thus obtained 2-tetralone derivative is represented by the general formula (1),

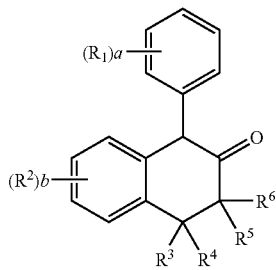

(1)

In the above general formula (1), "a", "b" and $R^1$ to $R^6$ are as defined in the above general formula (2).

The above 2-tetralone derivative is a compound which is useful as a starting material for the synthesis of, usually, steroids and various medicines.

Among the 2-tetralone derivatives of the invention represented by the above general formula (1), a compound represented by the following general formula (1'),

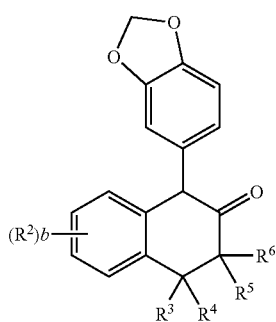

(1')

wherein "b" and $R^2$ to $R^6$ are as defined in the above general formula (1) or in the general formula (2), is a novel compound (in which a 1,3-dioxolan ring is formed by two groups $R^1$). This compound is useful not only as a starting material for the synthesis of intermediate products for various medicines but also as a starting material for the synthesis of chromene compounds having photochromic properties.

For instance, a naphthol derivative condensed with the 1,3-dioxolan ring is synthesized by using the compound of the formula (1'), and is reacted with the propargyl alcohol to synthesize a desired chromene compound.

In the above process, the scheme for synthesizing the naphthol derivative from the compound of the formula (1') is represented by the following formula. In the following scheme, a ring A represents the 1,3-dioxolan ring, a ring B represents the tetralin ring, and the substituents $R^2$ to $R^6$ have not been shown.

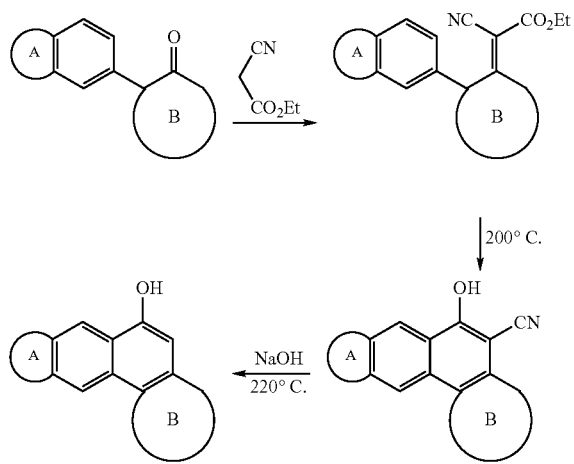

As will be understood from the above scheme of synthesis, the 2-tetralone derivative of the formula (1') is reacted with an ethyl cyanoacetate ($CNCH_2CO_2Et$) in a suitable organic solvent, followed by heating at about 200° C. to close the ring so as to form a naphthol ring condensed with the 1,3-dioxolan ring. Thereafter, an alkali hydroxide such as NaOH is added thereto followed by heating at about 220° C. to remove the cyano group bonded to the naphthol ring by melting with alkali. Thus, the naphthol derivative condensed with the 1,3-dioxolan ring is obtained.

The propargyl alcohol to be reacted with the thus obtained naphthol derivative is represented by the following general formula (3),

(3)

wherein $R^9$ and $R^{10}$ may be the same or different and are, respectively, alkyl groups, aryl groups or heteroaryl groups.

In the propargyl alcohol of the above general formula (3), though there is no particular limitation, the alkyl group is, generally, the one having not more than 4 carbon atoms, such as methyl group, ethyl group, n-propyl group, isopropyl group, n-butyl group, sec-butyl group or t-butyl group. The aryl group is, preferably, the one having 6 to 14 carbon atoms, such as phenyl group or naphthyl group. Though there is no particular limitation, the heteroaryl group includes oxygen, sulfur or nitrogen atom as a hetero atom, and will be the one having 4 to 12 atoms that form the ring, such as thienyl group, furyl group, pyrrolinyl group, pyridyl group, benzothienyl group, benzofuranyl group, benzopyrrolinyl group and julolidino group. Further, the above alkyl group may have a halogen atom or amino group as a substituent. Moreover, the aryl group and heteroaryl group, too, may have a halogen atom, amino group, alkyl group, cycloalkyl group or alkoxy group as a substituent.

The reaction of the naphthol derivative with the propargyl alcohol is conducted in the presence of an acid catalyst such as sulfuric acid, benzenesulfonic acid, p-toluenesulfonic acid or acidic alumina. The amount of the acid catalyst that is used may be a so-called catalytic amount and is, usually, about 0.1 to 10 parts by mass per 100 parts by mass of the total of the naphthol derivative and the propargyl alcohol. Further, there is no particular limitation on the ratio of amounts of the naphthol derivative and the propargyl alcohol; i.e., the amounts may be, generally, at an equimolar ratio. Further, the reaction temperature is about 0 to 200° C., and the reaction is conducted in a nonprotonic organic solvent, such as N-methylpyrrolidone, dimethylformamide, tetrahydrofuran, benzene or toluene.

Through the above reaction, a chromene compound represented by the following general formula (4) is obtained,

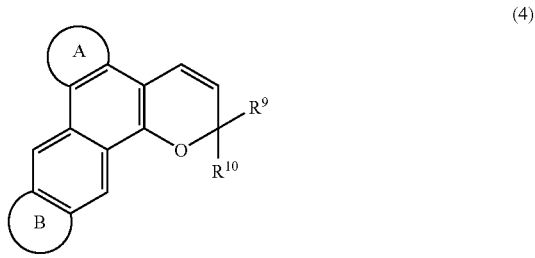

(4)

wherein $R^9$ and $R^{10}$ are as defined above, a ring "A" is the tetralin ring, a ring "B" is the 1,3-dioxolan ring, and substituents $R^2$ to $R^6$ are not shown.

The above chromene compound synthesized from the 2-tetralone derivative of the above general formula (1') has a structure condensed with the 1,3-dioxolan ring, and develop a neutral tint upon being irradiated with light, features quick color developing and fading rates, and has excellent light resistance.

EXAMPLES

Example 1

Synthesis of 1-(4-methoxyphenyl)-3,4-dihydro-1H-naphthalene-2-one 6.0 Grams (0.05 mols) of magnesium sulfate and 500 mL of toluene were added to 50.5 g (0.20 mols) of 7b-(4-methoxyphenyl)-1a,2,3,7b-tetrahydro-1-oxacyclopropa[a]naphthalene, and the mixture was heated at 80° C. for 2 hours. After cooled, the reaction product was washed two times each with 250 mL of water, and the organic layer was condensed under reduced pressure to obtain 1-(4-methoxyphenyl)-3,4-dihydro-1H-naphthalene-2-one represented by the following formula,

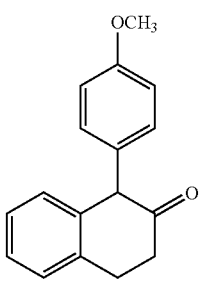

as pale yellow solid in an amount of 50.5 g (quantitative).

Example 2

Synthesis of 1-benzo[1,3]dioxole-5-yl-3,4-dihydro-1H-naphthalene-2-one 6.0 Grams (0.05 mols) of magnesium sulfate and 500 mL of toluene were added to 53.3 g (0.20 mols) of 7b-benzo[1,3]dioxole-5-yl-1a,2,3,7-tetrahydro-1-oxacyclopropa[a]naphthalene, and the mixture was heated at 80° C. for 2 hours. After cooled, the reaction product was washed two times each with 250 mL of water, and the organic layer was condensed under reduced pressure to obtain 1-benzo[1,3]dioxole-5-yl-3,4-dihydro-1H-naphthalene-2-one represented by the following formula,

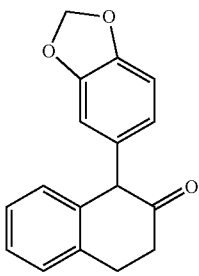

as a pale yellow oil in an amount of 53.3 g (quantitative).

Example 3

Synthesis of 6-methoxy-1-phenyl-3,4-dihydro-1H-naphthalene-2-one 6.0 Grams (0.05 mols) of magnesium sulfate and 500 mL of toluene were added to 50.5 g (0.20 mols) of 5-methoxy-7b-phenyl-1a,2,3,7b-tetrahydro-1-oxacyclopropa[a]naphthalene, and the mixture was heated at 80° C. for 2 hours. After cooled, the reaction product was washed two times each with 250 mL of water, and the organic layer was condensed under reduced pressure to obtain 6-methoxy-1-phenyl-3,4-dihydro-1H-naphthalene-2-one represented by the following formula,

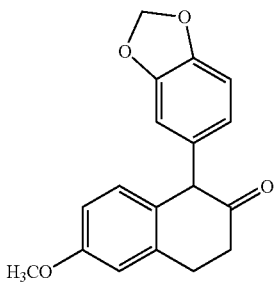

as pale yellow solid in an amount of 50.5 g (quantitative).

Example 4

Synthesis of 5-phenyl-7,8-dihydro-5H-naphtho[2,3-d][1,3]dioxole-6-one 6.0 Grams (0.05 mols) of magnesium sulfate and 500 mL of toluene were added to 53.3 g (0.20 mols) of 8b-phenyl-1a,2,3,8b-tetrahydro-1,5,7-trioxacyclopenta[g]cyclopropa[a]naphthalene, and the mixture was heated at 80° C. for 2 hours. After cooled, the reaction product was washed two times each with 250 mL of water, and the organic layer was condensed under reduced pressure to obtain 5-phenyl-7,8-dihydro-5H-naphtho[2,3-d][1,3]dioxole-6-one represented by the following formula,

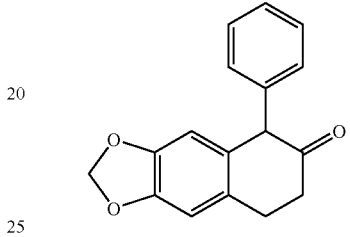

as pale yellow oil in an amount of 53.3 g (quantitative).

Example 5

Synthesis of 1-(4-methoxyphenyl-3-morpholino)-3,4-dihydro-1H-naphtalene-2-one 6.0 Grams (0.05 mols) of magnesium sulfate and 500 mL of toluene were added to 67.4 g (0.20 mols) of 7b-(4-methoxyphenyl-3-morpholino)-1a,2,3,7b-tetrahydro-1-oxacyclopropa[a]naphthalene, and the mixture was heated at 80° C. for 2 hours. After cooled, the reaction product was washed two times each with 250 mL of water, and the organic phase was condensed under reduced pressure to obtain 1-(4-methoxyphenyl-3-morpholino)-3,4-dihydro-1H-naphtalene-2-one represented by the following formula,

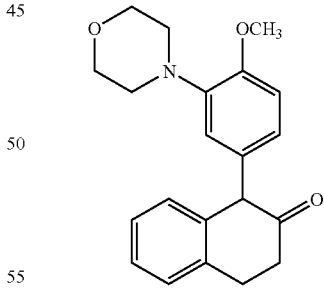

as a pale yellow solid in an amount of 67.4 g (quantitative).

Comparative Example 1

Synthesis of 1-benzo[1,3]dioxole-5-yl-3,4-dihydro-1H-naphtalene-2-one 500 mL of 30% sulfuric water solution was added to 53.3 g (0.20 mols) of 7b-benzo[1,3]dioxisole-5-yl-1a,2,3,7b-tetrahydro-1-oxacyclopropa[a]naphthalene, and the mixture was heated at 100° C. for 4 hours. After cooled, the reaction product was added to 500 ml toluene and was washed 6 times each with 500 mL of water, and the organic phase was condensed under reduced pressure to obtain 48.2 g of light brown oil. This oil contains impurities having a high polarity, therefore, the oil was refined with column chromatography using silica gel to obtain 1-benzo[1,3]dioxole-5-yl-3,4-dihydro-1H-naphtalene-2-one represented by the following formula,

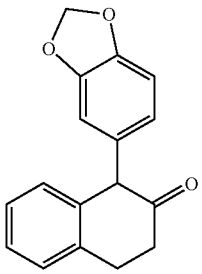

as pale yellow oil in an amount of 28.2 g (yield: 53%).

What we claim is:

1. A process for the preparation of a 1-aryl-3,4-dihydro-1H-naphthalene -2-one represented by the following general formula (1),

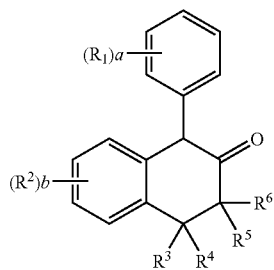

(1)

wherein a is an integer of 0 to 5, b is an integer of 0 to 4, $R^1$ and $R^2$ are alkyl groups, alkoxy groups, aralkoxy groups, substituted amino groups, cyano groups, halogen atoms, aralkyl groups or aryl groups, when a or b is 2 or more, a plurality of $R^1$ or $R^2$ may be different from each other, and two $R^1$ or $R^2$ at adjacent positions may be bonded together to form a divalent group represented by the following formula (1a), —(O)$_l$—(R$^7$O)$_m$—(R$^8$)$_n$—  (1a)

wherein $R^7$ and $R^8$ are alkylene groups, and l, m and n are, respectively, integers of 0 to 3 under a condition in which they are not all zero, and $R^3$ to $R^6$ are, respectively, hydrogen atoms, alkyl groups, alkoxy groups, aralkoxy groups, substituted amino groups, cyano groups, halogen atoms, aralkyl groups or aryl groups, comprising:

isomerizing epoxy compound (2) in an organic solvent in the presence of magnesium sulfate

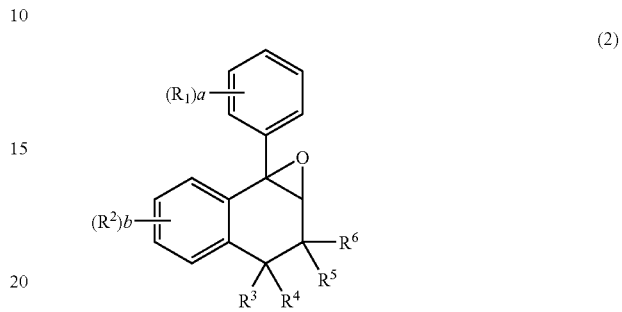

(2)

wherein a, b and $R^1$ to $R^6$ are as defined in the above general formula (1).

2. 1-aryl-3,4-dihydro-1H-naphthalene-2-one represented by the following general formula (1'),

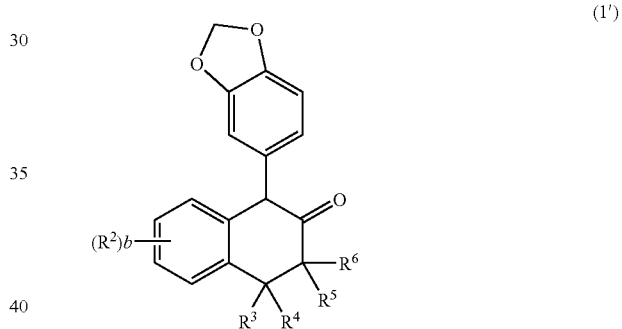

(1')

wherein b is an integer of 0 to 4, $R^2$ is an alkyl group, alkoxy group, aralkoxy group, substituted amino group, cyano group, halogen atom, aralkyl group or aryl group, and when b is 2 or more, a plurality of $R^2$ may be different from each other, and two $R^2$ at adjacent positions may be bonded together to form a divalent group represented by the following formula (1a), —(O)$_l$—(R$^7$O)$_m$—(R$^8$)$_n$—  (1a)

wherein $R^7$ and $R^8$ are alkylene groups, and l, m and n are, respectively, integers of 0 to 3 under a condition in which they are not all zero, and $R^3$ to $R^6$ are, respectively, hydrogen atoms, alkyl groups, alkoxy groups, aralkoxy groups, substituted amino groups, cyano groups, halogen atoms, aralkyl groups or aryl groups.

* * * * *